United States Patent
Pianca et al.

(10) Patent No.: US 9,162,055 B2
(45) Date of Patent: Oct. 20, 2015

(54) SYSTEMS AND METHODS FOR MAKING AND USING ELECTRODE CONFIGURATIONS FOR PADDLE LEADS

(75) Inventors: Anne Margaret Pianca, Santa Monica, CA (US); David Karl Lee Peterson, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 13/224,817

(22) Filed: Sep. 2, 2011

(65) Prior Publication Data

US 2012/0071948 A1 Mar. 22, 2012

Related U.S. Application Data

(60) Provisional application No. 61/383,643, filed on Sep. 16, 2010.

(51) Int. Cl.
*A61N 1/05* (2006.01)
*A61N 1/375* (2006.01)
*A61N 1/36* (2006.01)

(52) U.S. Cl.
CPC ............ *A61N 1/0553* (2013.01); *A61N 1/3752* (2013.01); *A61N 1/36071* (2013.01)

(58) Field of Classification Search
CPC .... A61N 1/046; A61N 1/0553; A61N 1/3605
USPC .................................. 607/116–117, 148, 152
See application file for complete search history.

(56) References Cited

U.S. PATENT DOCUMENTS

| | | | |
|---|---|---|---|
| 5,417,719 | A | 5/1995 | Hull |
| 6,181,969 | B1 | 1/2001 | Gord |
| 6,236,892 | B1 | 5/2001 | Feler |
| 6,516,227 | B1 | 2/2003 | Meadows et al. |
| 6,609,029 | B1 | 8/2003 | Mann et al. |
| 6,609,032 | B1 | 8/2003 | Woods et al. |
| 6,741,892 | B1 | 5/2004 | Meadows et al. |

(Continued)

FOREIGN PATENT DOCUMENTS

| | | |
|---|---|---|
| WO | 2007087626 A2 | 8/2007 |
| WO | WO 2007101999 A2 * | 9/2007 |
| WO | 2010028084 A2 | 3/2010 |

OTHER PUBLICATIONS

International Search Report and Written Opinion, PCT/US2011/050400, mailed Nov. 29, 2011.

*Primary Examiner* — Amanda Patton
(74) *Attorney, Agent, or Firm* — Lowe Graham Jones PLLC; Bruce E. Black

(57) ABSTRACT

A paddle lead assembly for providing electrical stimulation of patient tissue includes a paddle body having a longitudinal axis and a lateral axis transverse to the longitudinal axis. The paddle body includes a plurality of electrodes disposed into at least four columns extending parallel with the longitudinal axis. The at least four columns include two lateral columns and at least two medial columns disposed therebetween. The electrodes of the at least two medial columns are arranged into rows aligned along the transverse axis. The electrodes of the two lateral columns are each longitudinally offset from the rows of electrodes of the at least two medial columns. An array of terminals are disposed on each of at least one lead body coupled to the paddle body. A plurality of conductive wires couple each of the electrodes to at least one terminal of the terminal arrays.

25 Claims, 10 Drawing Sheets

(56) References Cited

U.S. PATENT DOCUMENTS

| | | |
|---|---|---|
| 7,244,150 B1 | 7/2007 | Brase et al. |
| 7,289,846 B2 | 10/2007 | Shoberg |
| 7,437,193 B2 | 10/2008 | Parramon et al. |
| 7,672,734 B2 | 3/2010 | Anderson et al. |
| 7,761,165 B1 | 7/2010 | He et al. |
| 7,904,161 B2 * | 3/2011 | Osypka ............................ 607/37 |
| 7,949,395 B2 | 5/2011 | Kuzma |
| 7,974,706 B2 | 7/2011 | Moffitt et al. |
| 8,774,941 B2 | 7/2014 | Pianca |
| 2005/0165465 A1 | 7/2005 | Pianca et al. |
| 2007/0150036 A1 | 6/2007 | Anderson |
| 2007/0219595 A1 | 9/2007 | He |
| 2007/0255372 A1 | 11/2007 | Metzler et al. |
| 2008/0071320 A1 | 3/2008 | Brase |
| 2008/0269856 A1 | 10/2008 | Cross et al. |
| 2009/0187221 A1 | 7/2009 | DiGiore |
| 2010/0057176 A1 | 3/2010 | Barker |
| 2010/0057177 A1 * | 3/2010 | Moffitt et al. ................. 607/117 |
| 2010/0070010 A1 | 3/2010 | Simpson |
| 2010/0100165 A1 | 4/2010 | Swanson et al. |
| 2010/0137943 A1 | 6/2010 | Zhu |

* cited by examiner

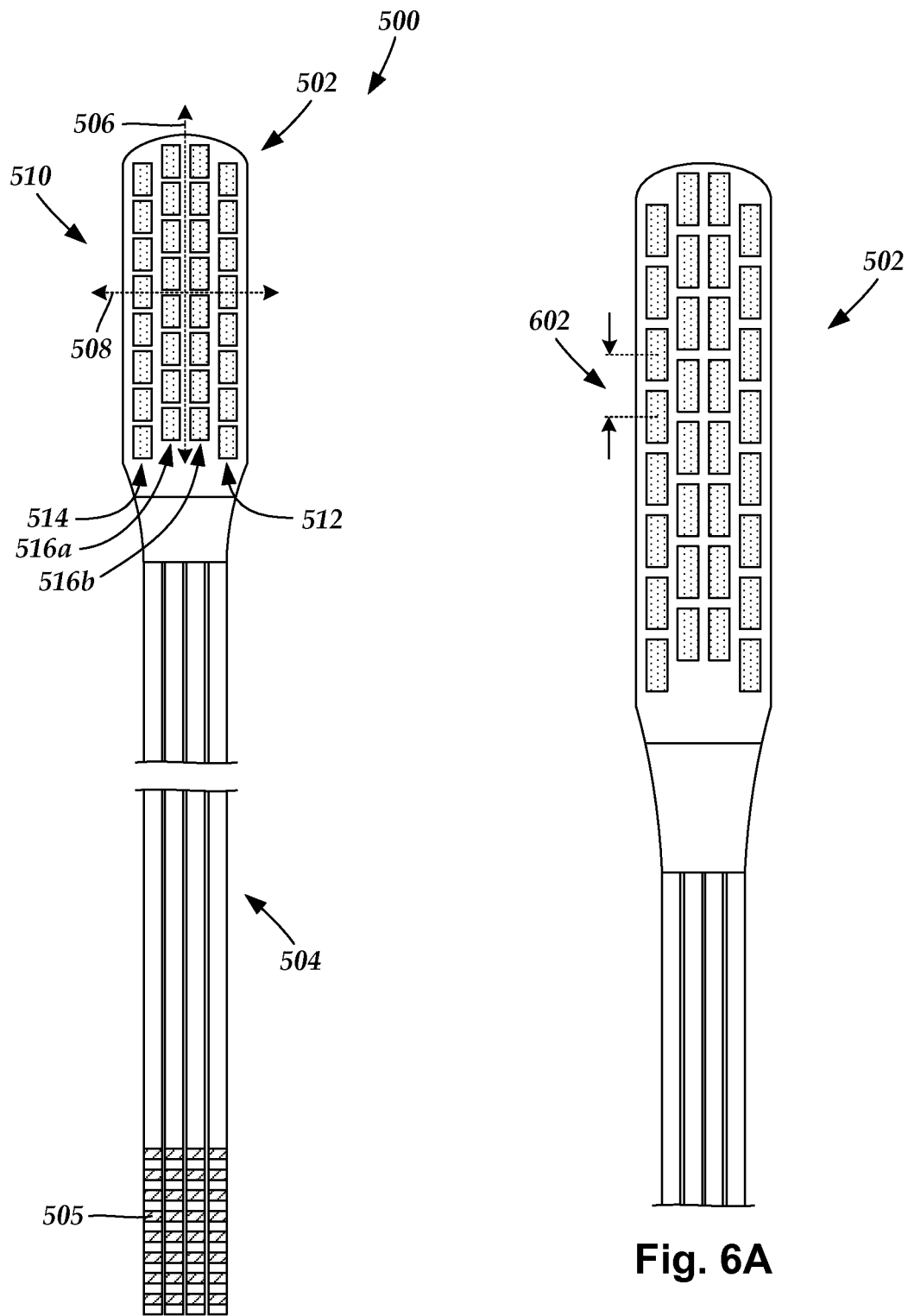

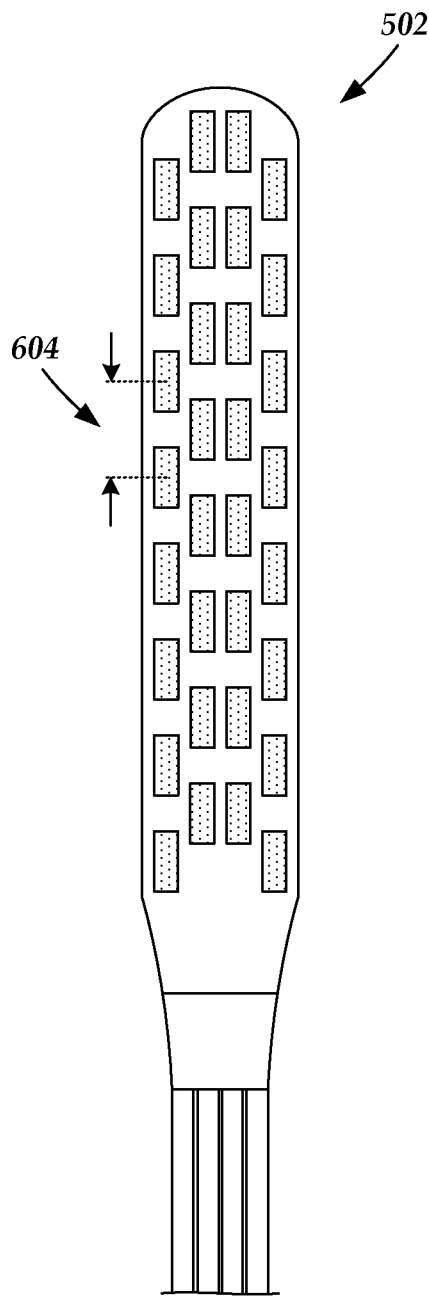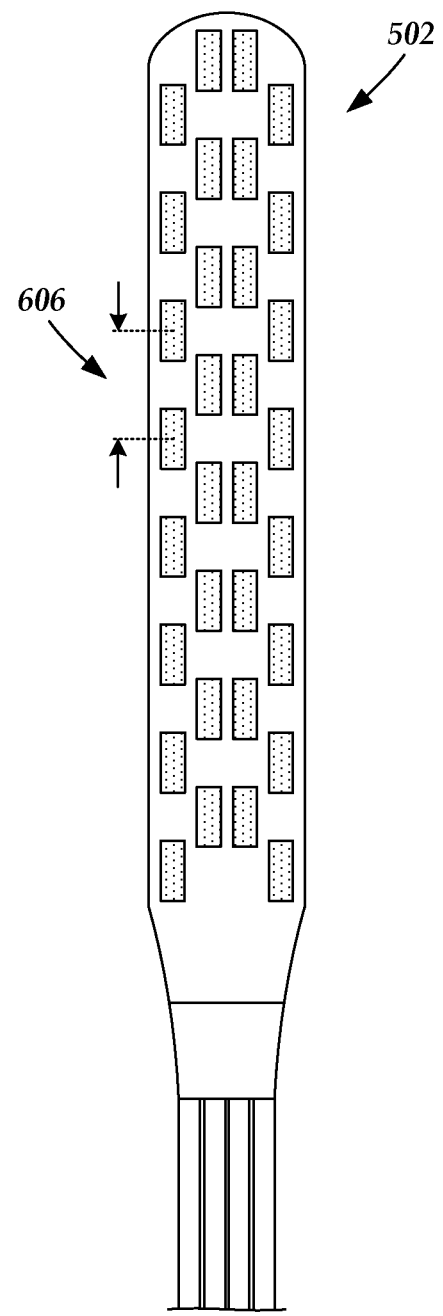
Fig. 6B
Fig. 6C

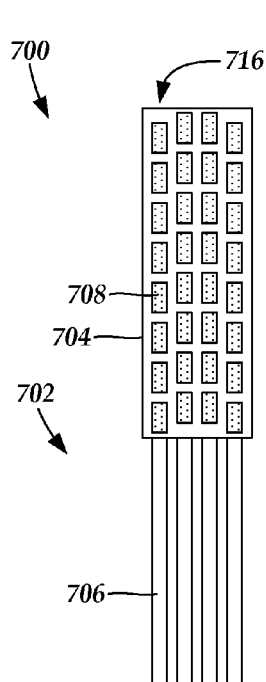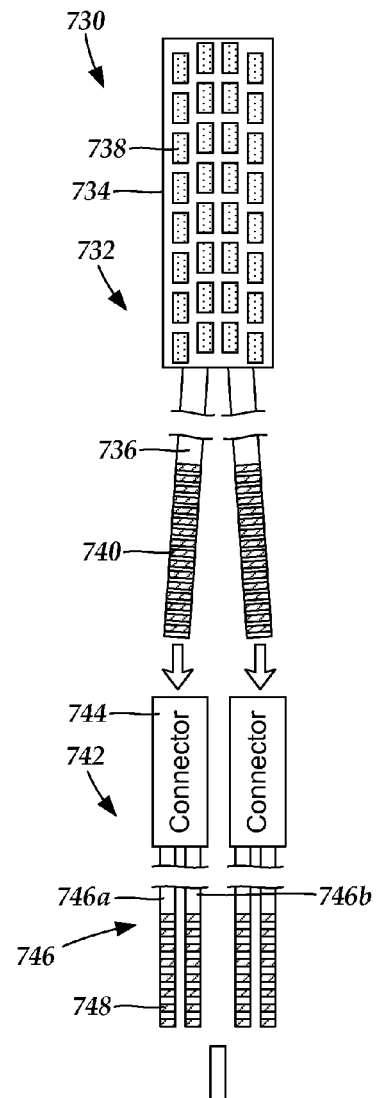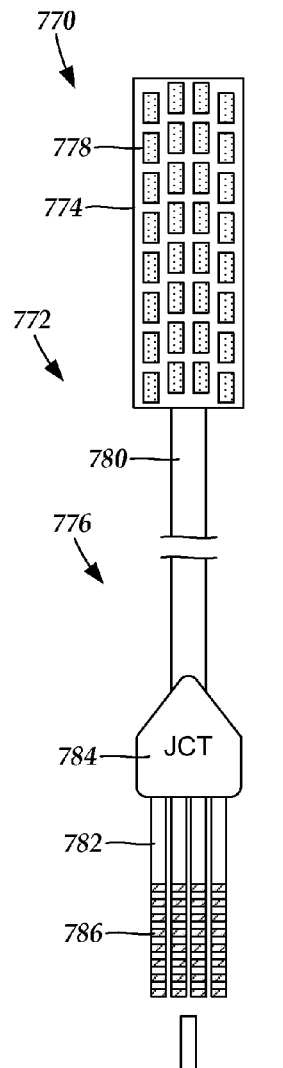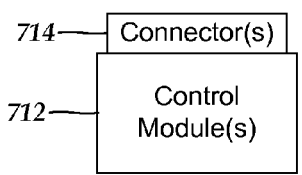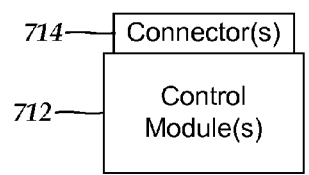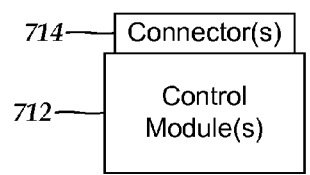
Fig. 7A         Fig. 7B         Fig. 7C

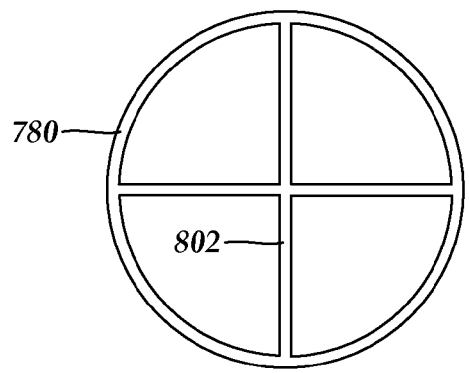
Fig. 8A
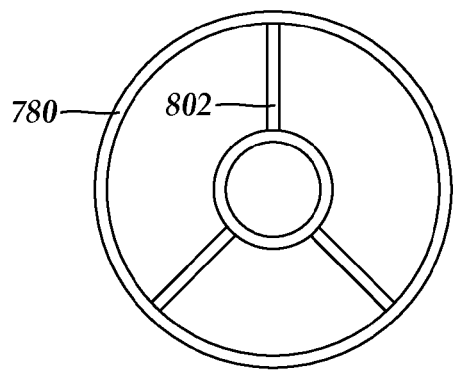
Fig. 8B
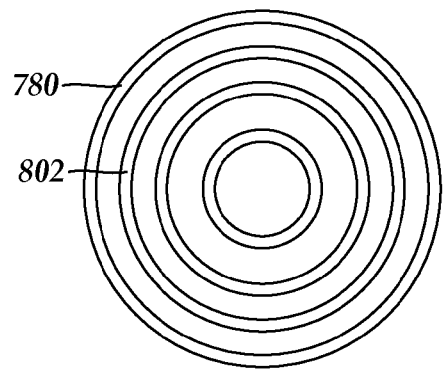
Fig. 8C
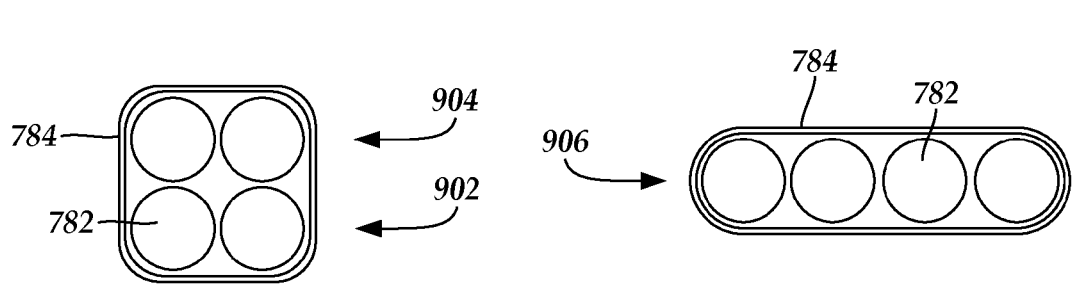
Fig. 9A
Fig. 9B

SYSTEMS AND METHODS FOR MAKING AND USING ELECTRODE CONFIGURATIONS FOR PADDLE LEADS

CROSS-REFERENCE TO RELATED APPLICATIONS

This application claims the benefit under 35 U.S.C. §119 (e) of U.S. Provisional Patent Application Ser. No. 61/383,643 filed on Sep. 16, 2010, which is incorporated herein by reference.

FIELD

The present invention is directed to the area of implantable electrical stimulation systems and methods of making and using the systems. The present invention is also directed to implantable electrical stimulation paddle leads that include electrodes configured into arrangements that improve control of stimulation, as well as methods of making and using the paddle leads, electrodes, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a paddle lead assembly for providing electrical stimulation of patient tissue includes a paddle body having a longitudinal axis and a lateral axis transverse to the longitudinal axis. The paddle body includes a plurality of electrodes disposed into at least four columns extending parallel with the longitudinal axis. The at least four columns include two lateral columns and at least two medial columns disposed therebetween such that the two lateral columns flank the at least two medial columns. The electrodes of the at least two medial columns are arranged into rows aligned along the transverse axis. The electrodes of the two lateral columns are each longitudinally offset from the rows of electrodes of the at least two medial columns. A plurality of lead bodies are coupled to the paddle body. An array of terminals are disposed on each of the at least one lead bodies. The paddle lead assembly further includes a plurality of conductive wires, each conductive wire coupling one of the electrodes to at least one terminal of at least one of the terminal arrays.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 5 is a schematic top view of one embodiment of a paddle lead assembly that includes a paddle body with four columns of electrodes, according to the invention;

FIG. 6A is a schematic top view of another embodiment of the paddle body of FIG. 5, according to the invention;

FIG. 6B is a schematic top view of yet another embodiment of the paddle body of FIG. 5, according to the invention;

FIG. 6C is a schematic top view of another embodiment of the paddle body of FIG. 5, according to the invention;

FIG. 7A is a schematic view of one embodiment of a paddle lead assembly of an electrical stimulation system, according to the invention;

FIG. 7B is a schematic view of a second embodiment of a paddle lead assembly of an electrical stimulation system, according to the invention;

FIG. 7C is a schematic view of a third embodiment of a paddle lead assembly of an electrical stimulation system, according to the invention;

FIG. 8A is a schematic transverse cross-sectional view of one embodiment of an intermediate extension element of a lead body arrangement of the paddle lead assembly of FIG. 7C, according to the invention;

FIG. 8B is a schematic transverse cross-sectional view of another embodiment of an intermediate extension element of a lead body arrangement of the paddle lead assembly of FIG. 7C, according to the invention;

FIG. 8C is a schematic transverse cross-sectional view of yet another embodiment of an intermediate extension element of a lead body arrangement of the paddle lead assembly of FIG. 7C, according to the invention;

FIG. 9A is a schematic transverse cross-sectional view of one embodiment of a multi-layer arrangement of lead bodies disposed in a junction of the paddle lead assembly of FIG. 7C, according to the invention;

FIG. 9B is a schematic transverse cross-sectional view of another embodiment of a one-layer arrangement of lead bodies disposed in a junction of the paddle lead assembly of FIG. 7C, according to the invention;

DETAILED DESCRIPTION

The present invention is directed to the area of implantable electrical stimulation systems and methods of making and using the systems. The present invention is also directed to implantable electrical stimulation paddle leads that include electrodes configured into arrangements that improve control of stimulation, as well as methods of making and using the paddle leads, electrodes, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; 7,244,150; 7,672,734; 7,761,165; 7,949,395; 7,974,706; and U.S. Patent Applications Publication Nos. 2005/0165465; 2007/0150036; 2007/0219595; and 2008/0071320, all of which are incorporated by reference.

Figure 1:
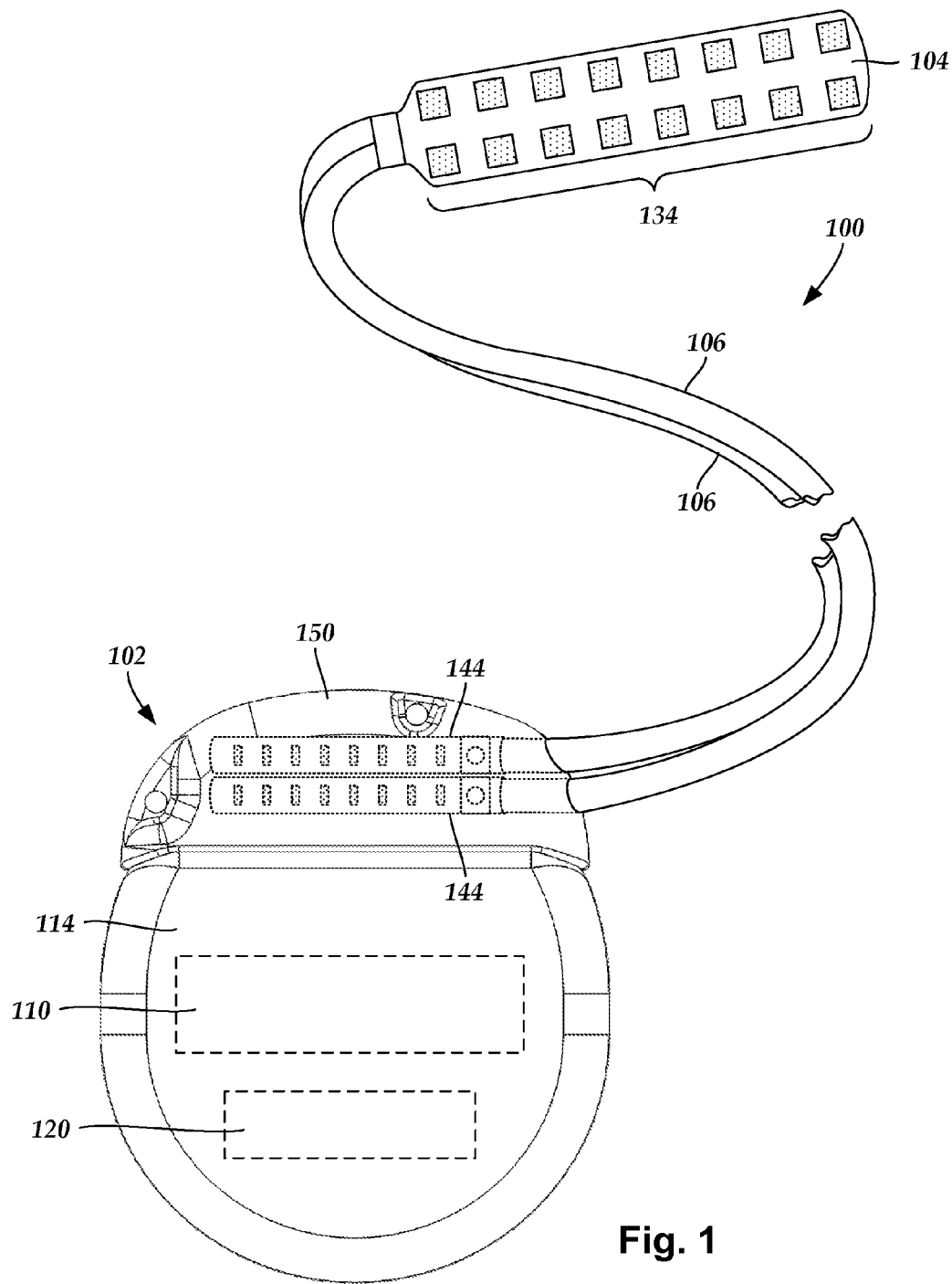
FIG. 1 is a schematic view of one embodiment of an electrical stimulation system that includes a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

Figure 2A:
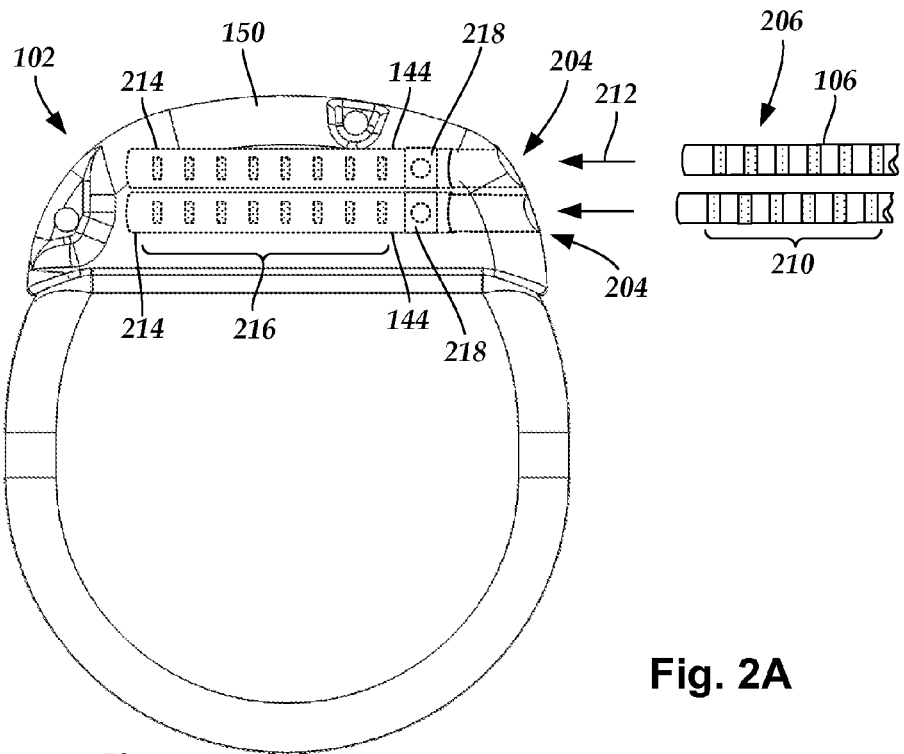
FIG. 2A is a schematic side view of one embodiment of a plurality of connector assemblies disposed in the control module of FIG. 1, the connector assemblies configured and arranged to receive the proximal portions of the lead bodies of FIG. 1, according to the invention.

The control module 102 typically includes one or more connector assemblies 144 into which the proximal end of the one or more lead bodies 106 can be plugged to make an electrical connection via connector contacts (e.g., 216 in FIG. 2A). The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 224 (see FIG. 2B) can be disposed between the one or more lead bodies 106 and the control module 102 to extend the distance between the one or more lead bodies 106 and the control module 102.

The electrical stimulation system or components of the electrical stimulation system, including one or more of the lead bodies 106, the paddle body 104, and the control module 102, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium nitride, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 210 in FIG. 2A) are typically disposed at the proximal end of the one or more lead bodies 106 for connection to corresponding conductive contacts (e.g., 216 in FIG. 2A) in connector assemblies disposed on, for example, the control module 102 (or to other devices, such as conductive contacts on a lead extension, an operating room cable, a splitter, an adaptor, or the like). Conductive wires (not shown) extend from the terminals to the electrodes 134. Typically, one or more electrodes 134 are electrically coupled to a terminal (e.g., 210 in FIG. 2A). In some embodiments, each terminal (e.g., 210 in FIG. 2A) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient.

Additionally, there may also be one or more lumens (not shown) that open at, or near, the distal end of the lead, for example, for infusion of drugs or medication into the site of implantation of the paddle body 104. The one or more lumens may, optionally, be flushed continually, or on a regular basis, with saline, epidural fluid, or the like. The one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

FIG. 2A is a schematic side view of one embodiment of the two lead bodies 106 shown in FIG. 1 configured and arranged for coupling with the control module 102. A plurality of connector assemblies 144 are disposed in the control module 102. In at least some embodiments, the control module 102 includes two, three, four, or more connector assemblies 144. Typically, the number of connector assemblies 144 disposed in the control module 102 is equal to the number of lead bodies 106 of the lead. For example, in FIG. 2A, the two lead bodies 106 shown in FIG. 1 are shown configured and arranged for insertion into two connector assemblies 144 disposed on the control module 102.

The connector assemblies 144 each include a connector housing 214 and a plurality of connector contacts 316 disposed therein. Typically, the connector housing 214 defines a port (not shown) that provides access to the plurality of connector contacts 216. In at least some embodiments, the connector assemblies 144 further include retaining elements 218 configured and arranged to fasten the corresponding lead bodies 206 to the connector assemblies 144 when the lead bodies 106 are inserted into the connector assemblies 144 to prevent undesired detachment of the lead bodies 106 from the connector assemblies 144. For example, the retaining elements 218 may include apertures through which fasteners (e.g., set screws, pins, or the like) may be inserted and secured against an inserted lead body (or lead extension).

In FIG. 2A, the plurality of connector assemblies 144 are disposed in the header 150. In at least some embodiments, the header 150 defines one or more ports 204 into which a proximal end 206 of the one or more lead bodies 106 with terminals 210 can be inserted, as shown by directional arrows 212, in order to gain access to the connector contacts 216 disposed in the connector assemblies 144.

When the lead bodies 106 are inserted into the ports 204, the connector contacts 216 can be aligned with the terminals 210 disposed on the lead bodies 106 to electrically couple the control module 102 to the electrodes (134 of FIG. 1) disposed at a distal end of the lead bodies 106. Examples of connector assemblies in control modules are found in, for example, U.S. Pat. No. 7,244,150 and U.S. Patent Application Publication No. 2008/0071320 A1, which are incorporated by reference.

In some instances, the electrical stimulation system may include one or more lead extensions. FIG. 2B is a schematic side view of one embodiment of a proximal end of a single lead body 106' configured and arranged to couple with a lead extension 224 that is coupled with the control module 102'. In FIG. 2B, a lead extension connector assembly 222 is disposed at a distal end 226 of the lead extension 224. The lead extension connector assembly 222 includes a contact housing 228. The contact housing 228 defines at least one port 230 into which a proximal end 206 of the lead body 106' with terminals 210 can be inserted, as shown by directional arrow 238. The lead extension connector assembly 222 also includes a plurality of connector contacts 240. When the lead body 106' is inserted into the port 230, the connector contacts 240 disposed in the contact housing 228 can be aligned with the terminals 210 on the lead body 106 to electrically couple the lead extension 224 to electrodes (not shown) disposed on the lead body 106'.

The proximal end of a lead extension can be similarly configured and arranged as a proximal end of a lead body, such as one of the lead bodies 106, or the lead body 106'. The lead extension 224 may include a plurality of conductive wires (not shown) that electrically couple the connector contacts 240 to terminals at the proximal end 248 of the lead extension 224. The conductive wires disposed in the lead extension 224 can be electrically coupled to a plurality of terminals (not shown) disposed on the proximal end 248 of the lead extension 224.

Figure 2C:
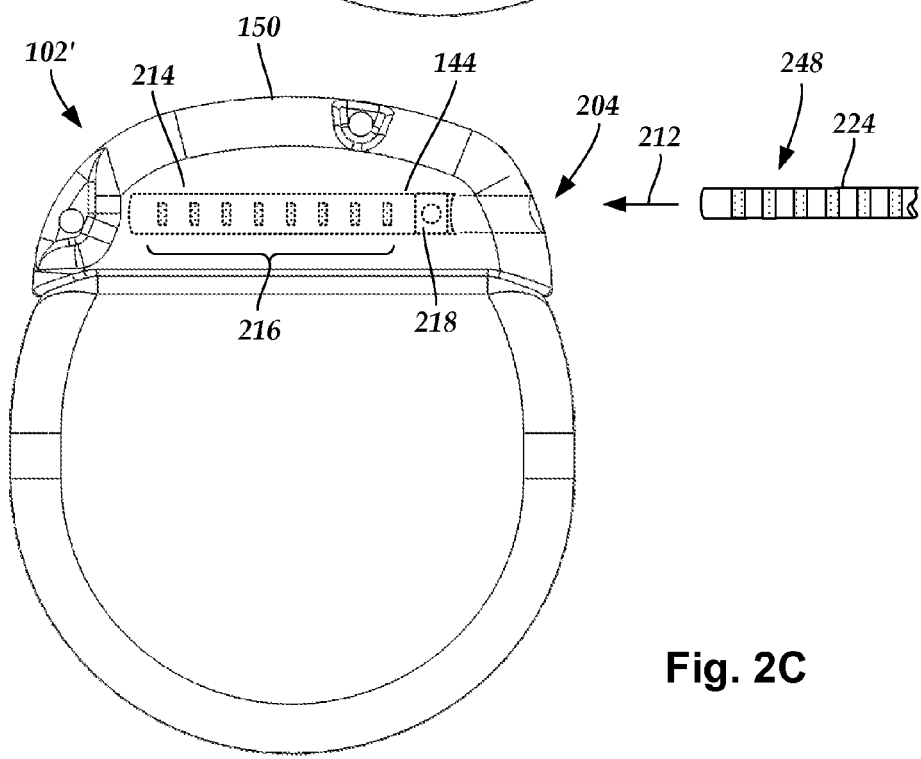
FIG. 2C is a schematic side view of one embodiment of a connector assembly disposed in the control module of FIG. 2B, the connector assembly configured and arranged to receive the lead extension of FIG. 2B, according to the invention.
Figure 2B:
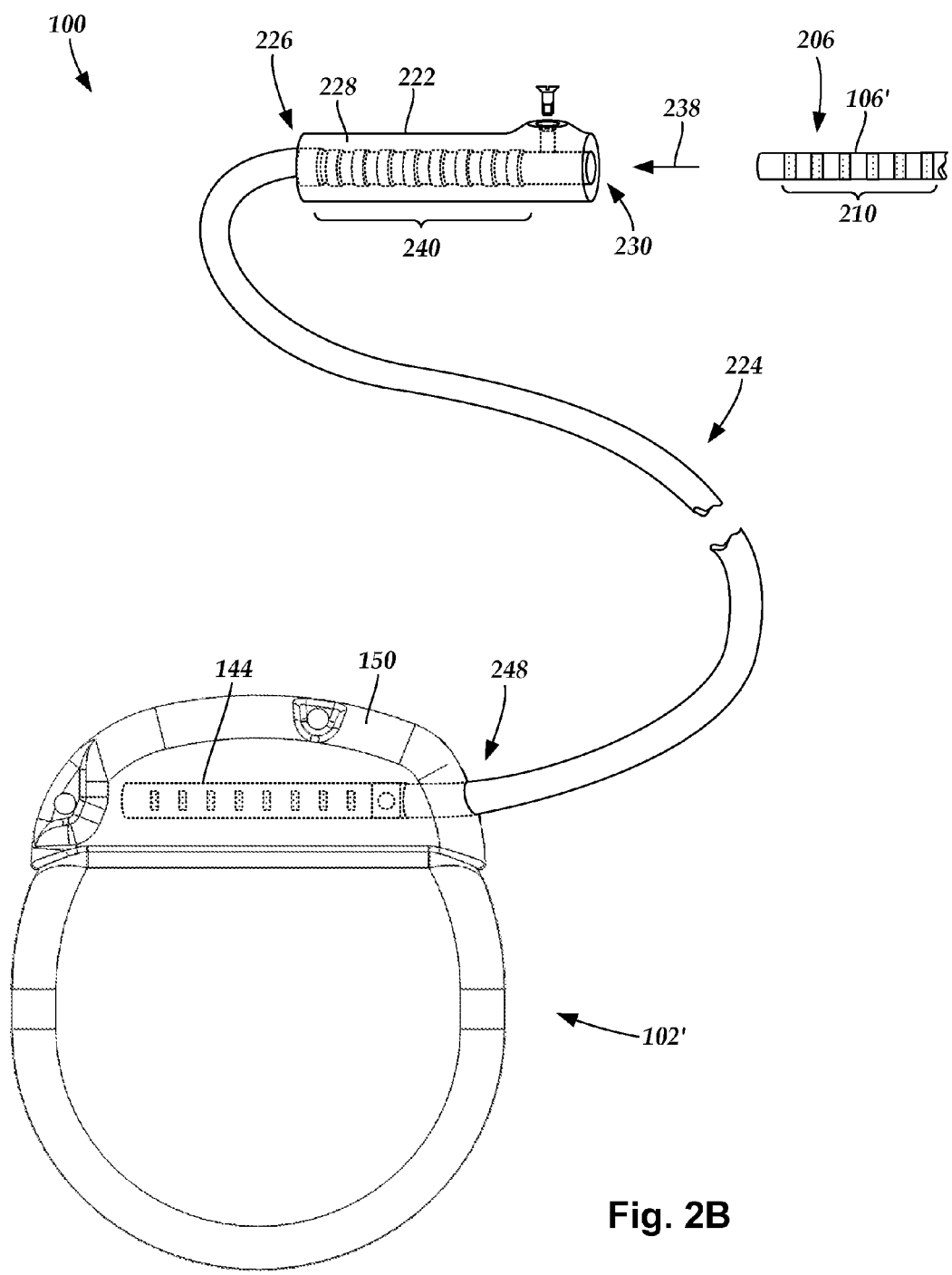
FIG. 2B is a schematic side view of one embodiment of a proximal portion of a lead body and a lead extension coupled to a control module, the lead extension configured and arranged to couple the proximal portion of the lead body to the control module, according to the invention.

FIG. 2C is a schematic side view of one embodiment of the lead extension 224 configured and arranged for coupling with the control module 102'. The control module 102' includes a single connector assembly 144. Alternately, the control module 102' may receive the lead body 106' directly. It will be understood that the control modules 102 and 102' can both receive either lead bodies or lead extensions. It will also be understood that the electrical stimulation system 100 can include a plurality of lead extensions 224. For example, each of the lead bodies 106 shown in FIGS. 1 and 2A can, alternatively, be coupled to a different lead extension 224 which, in turn, are each coupled to different ports of a two-port control module, such as the control module 102 of FIGS. 1 and 2A.

Figure 3:
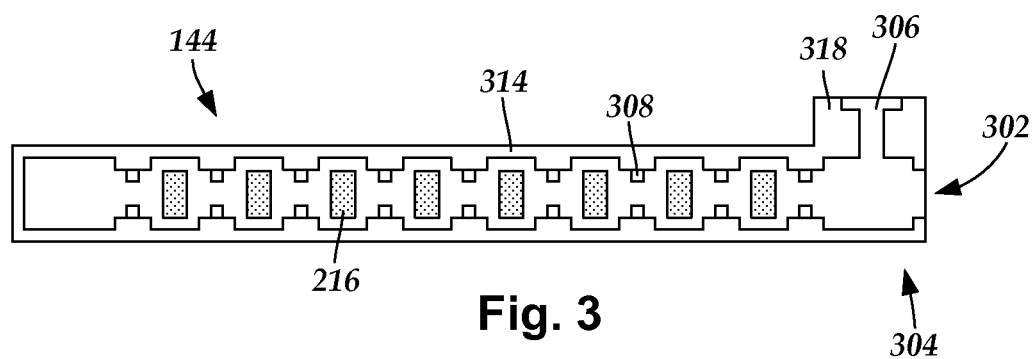
FIG. 3 is a schematic longitudinal cross-sectional view of one embodiment of one of the connector assemblies of FIG. 1, according to the invention.

FIG. 3 is a schematic longitudinal cross-sectional view of one embodiment of one of the connector assemblies 144. The connector assembly 144 includes the connector housing 314 into which a lead or lead extension can be inserted via a port 302 at a distal end 304 of the connector housing 314. In at least some embodiments, a retaining element 318 is coupled to the connector housing 314. The retaining element 318 defines an aperture 306 through which a fastener (e.g., a set screw, pin, or the like) may be inserted and secured against a lead body or lead extension when the lead or lead extension is inserted into the port 302. Connector contacts, such as the connector contact 216, are disposed in the connector housing 314. In at least some embodiments, each of the connector assemblies 144 includes eight connector contacts.

The connector contacts 216 may be separated from one another by one or more non-conductive spacers (or seals), such as spacer 308, to prevent electrical contact between adjacent connector contacts 216. As discussed above, when a proximal end of a lead or lead extension is inserted into the port 302, terminals disposed on the inserted lead or lead extension align with the connector contacts 216, thereby establishing an electrical connection between the electronic subassembly 110 of the control module 102 and the electrodes 134 of the lead.

Figure 4:
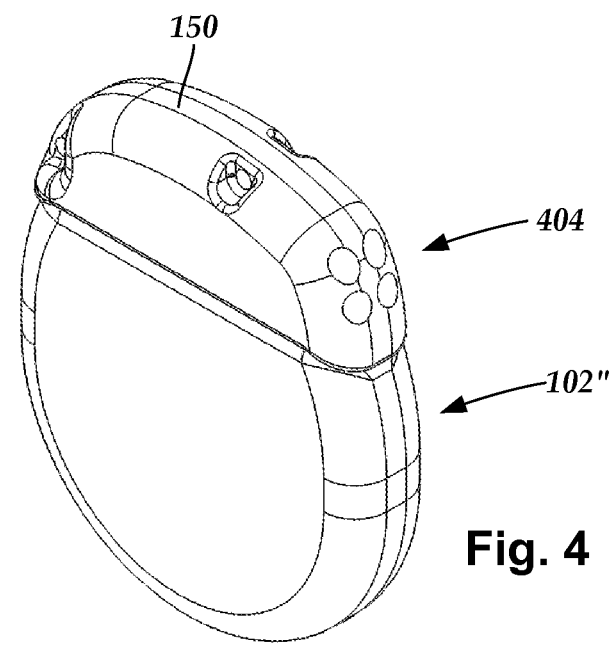
FIG. 4 is a schematic perspective view a control module with a header that defines four ports, according to the invention.

FIG. 4 is a schematic perspective view of a control module 102". The header 150 of the control module 102" defines four header ports 404. Collectively, the header ports 404 are configured and arranged to each receive one or more lead bodies 106 or one or more lead extensions (e.g., lead extension 324 of FIG. 3B), or both. The header 150 can define any suitable number of header ports 404 including, for example, one, two, three, four, five, six, seven, eight, or more header ports 404. In FIG. 4, the header 150 is shown defining four header ports 404. Thus, in at least some embodiments, the control module 102 of FIG. 4 is configured and arranged to receive up to four lead bodies 106 or lead extensions 224, or a combination of both.

The header ports 404 can be defined in the header 150 in any suitable arrangement. In preferred embodiments, each of the header ports 404 are configured and arranged to align with one of the ports 302 of the one or more connector assemblies 144 disposed in the header 150. For example, in at least some embodiments, four connector assemblies 144 are disposed in the header 150 such that four header ports 404 defined in the header 150 align with the four ports 302 of the four connector assemblies 144. In at least some embodiments, the number of header ports 404 is no greater than the number of connector assemblies 144. In at least some embodiments, the number of header ports 404 is no less than the number of connector assemblies 144. In at least some embodiments, the number of header ports 404 is equal to the number of connector assemblies 144.

It may be useful to design a lead with more electrodes than the lead illustrated in FIG. 1. For example, a patient may be experiencing pain emanating from an area greater in size than the dimensions of an array of electrodes (e.g., 134 of FIG. 1) disposed on the distal end of a conventional paddle lead. It may further be useful to selectively target one or more separately-situated stimulation regions (e.g., nerve fibers, or the like) along the spinal cord while reducing, or even eliminating, stimulation of other regions in proximity to the stimulation regions.

Paddle bodies are typically surgically implanted into a patient. The location of implantation may have some impact on the design (e.g., the size, shape, or the like) of the paddle body. For example, when the one or more target stimulation regions are along the spinal cord of the patient, the paddle body is typically surgically implanted into the epidural space of the patient. It may, therefore, be an advantage to form the paddle body to fit within the confines of the patient's epidural space.

Typically, the paddle body is implanted into the epidural space such that a longitudinal axis of the paddle body is positioned along a rostral-caudal axis (i.e., head to toe) of the patient, and an axis transverse to the longitudinal axis (a "width") is positioned along a medial-lateral axis (i.e., shoulder to shoulder) of the patient. Therefore, it may be an advantage to form the paddle body with a width that is narrow enough to fit within the medial-lateral confines of the epidural space without causing undue discomfort to the patient.

Forming the paddle body width to be narrow enough to fit within the epidural space, however, may limit the amount of space onto which electrodes can be disposed. Increasing the number of electrodes disposed on the paddle lead may, therefore, also involve decreasing the spacing between adjacent electrodes on the paddle body. As the spacing between electrodes decreases, an increase in current shunting may occur between at least some electrodes. Current shunting may adversely affect the amplitude of stimulation of affected electrodes by decreasing the depth of current penetration. Current shunting, however, can also be used to facilitate tuning of the direction of stimulation.

Other techniques, such as current steering, may also be used to facilitate tuning of the direction of stimulation. Sometimes, one or more electrodes of an electrode array are configured and arranged to operate as cathodes, while one or more other electrodes of the electrode array are configured and arranged to operate as anodes. Current steering may involve applying disproportionate amounts of current to two or more adjacent cathodes.

In at least some embodiments, the longitudinal spacing between adjacent electrodes is selected for improving medial-lateral current steering. In at least some embodiments, the longitudinal spacing between adjacent electrodes is selected for improving a span of rostral-caudal stimulation. In at least some embodiments, the anodes and cathodes are arranged on the paddle body such that they reduce, or even eliminate, undesired stimulation of nerve fibers of the dorsal root. In at least some embodiments, lateral columns of corresponding anodes are longitudinally offset from the longitudinally-aligned cathodes in order to increase spacing between corresponding anodes and cathodes without increasing the width of the paddle body.

FIG. 5 is a top schematic view of one embodiment of a paddle lead assembly 500. The paddle lead assembly 500 includes a paddle body 502 and a plurality of lead bodies 504. At least some of the plurality of lead bodies 504 include arrays of terminals 505. In at least some embodiments, terminal arrays 505 are disposed on each of the plurality of lead bodies 504.

The paddle body 502 includes a longitudinal axis 506 and a transverse axis 508 that is transverse to the longitudinal axis 506. The paddle body 502 includes an array of electrodes 510. The paddle body 502 can include any number of electrodes in the electrode array 510 including, for example, sixteen, eighteen, twenty, twenty-two, twenty-four, twenty-six, twenty-eight, thirty, thirty-two, thirty-four, or more electrodes. It will be understood that other numbers of electrodes may be used instead.

Individual electrodes within the electrode array 510 are arranged into columns extending parallel with the longitudinal axis 506 of the paddle body 502. The columns of electrodes include lateral columns 512 and 514. The columns of electrodes also include two or more medial columns 516. In FIG. 5, the paddle body 502 is shown with two medial columns 516a and 516b. In at least some embodiments, the medial columns 516a and 516b of electrodes are staggered longitudinally relative to the two lateral columns 512 and 514.

Each of the columns 512, 514, 516 of the electrode array 510 may include the same number of electrodes. In at least some embodiments, at least one of the columns 512, 514, 516 of the electrode array 510 include a different number of electrodes from one or more of the other columns. In at least some embodiments, each of the lateral columns, 512 and 514, include the same number of electrodes. In at least some embodiments, each of the two or more medial columns 516 include the same number of electrodes. In at least some embodiments, the total number of electrodes disposed in the lateral columns 512, 514 is equal to the total number of electrodes disposed in the two or more medial columns 516. In at least some embodiments, each of the lateral columns, 512 and 514, include the same number of electrodes, while each of the two or more medial columns 516 also include the same number of electrodes, where the number of electrodes disposed in the lateral columns 512 and 514 is different from the number of electrodes disposed in the two or more medial columns 516.

In FIG. 5, each of the columns 512, 514, 516a, 516b of the electrode array 510 is shown having eight electrodes. It will be understood that other numbers of electrodes, either fewer or greater, may be disposed in each column. For example, each of the columns 512, 514, 516 can include two, three, four, five, six, seven, eight, nine, ten, eleven, twelve, thirteen, fourteen, fifteen, sixteen, seventeen, eighteen, nineteen, twenty, twenty-four, thirty-two or more electrodes.

Each of the electrodes of the electrode array 510 may be independently operated, via a pulse generator disposed in the control module 102. In at least some embodiments, the control module 102 has at least as many independently programmable stimulation channels as electrodes in the electrode array 510. The control module 102 stimulation channels may be independently programmable, preferably to deliver constant current stimulus pulses to each of the electrodes of the electrode array 510. The constant current stimulus pulses may be biphasic in form.

A cathodic (current) stimulus pulse can have a negative square wave spike followed by a longer duration positive return that causes the biphasic stimulus to be charged balanced. The cathodic spike is the portion of the current stimulus that causes nerve tissues to be stimulated and discharged, causing an action potential to propagate along the nerve. When the electrical stimulation system has thirty-two electrodes in the electrode array 510, and 32 independently programmable channels in the control module 102, each of the electrodes of the array 510 may function as a cathode, as an anode, or be effectively turned off at any point in time. When a biphasic cathodic stimulus pulse is delivered through a particular electrode of the electrode array 510, that particular electrode is referred to as a "cathode." When the same particular electrode is functioning in the opposite polarity (a positive spike followed by longer duration negative return), that particular electrode is referred to as an "anode." The use of the term "cathode" or "anode" as used herein, refers to whether the particular electrode in the paddle body that is delivering a biphasic stimulus pulse is sinking or sourcing the stimulus current.

Turning back to FIGS. 3 and 4 (in combination with FIG. 5), in at least some embodiments four connector assemblies 144 are disposed in the header 150 and accessible to up to four lead bodies 505 via four header ports 404. Each port 302 defined in the connector assemblies 144 can be configured and arranged to enable an electrical connection between the terminals 505 of the lead bodies 504. In at least some embodiments, each port (302 of FIG. 3) of the connector assemblies (144 of FIG. 3) has eight connector contacts. In at least some embodiments, the control module (102" in FIG. 4) has a total of 32 independently programmable stimulation channels.

Each channel may be programmed to operate as a cathode, an anode, or be turned off at any one time. Additionally, each stimulus channel may sink different magnitudes of stimulus current through two or more cathode electrodes and source stimulus current with different magnitudes through two or more anodes. Moreover, the housing (114 in FIG. 1) of the control module 102 can be programmed to be an anode or to be OFF. When the electrical stimulation system includes a 32-contact paddle assembly 500, the control module 102 may also enable many different configurations of monopolar stimulation (i.e., one or more of the electrodes in the electrode array 510 may concurrently be delivering a cathodic stimulus pulse, while the remainder of the electrodes are OFF and the housing (114 of FIG. 1) of the control module 102 is turned on as the anode).

Additionally, the stimulation system may also enable many different configurations of multipolar stimulation (i.e., one or more of the electrodes in the electrode array 510 may function as cathodes and, concurrently, one or more of the electrodes 510 may function as anodes). Alternatively, it may be possible to have a hybrid stimulation system (i.e., one or more of the electrodes in the electrode array 510 is functioning as an anode and, concurrently, the housing (114 of FIG. 1) of the control module may be functioning as an anode).

At least some potential implantation sites within the epidural space include both sensory and motor nerve fibers. In at least some embodiments, it is generally preferred to stimulate sensory nerve fibers without unduly stimulating motor nerve fibers, which may potentially cause undesired motor movements. Therefore, in at least some embodiments, when the paddle body 502 is disposed in the epidural space, it is generally preferred to position the electrode array 510 to stimulate nerve fibers in the dorsal column (primarily sensory nerve fibers) while avoiding stimulation of nerve fibers in the dorsal roots (both sensory and nerve fibers). It will be understood that, in alternate embodiments, the paddle body 502 can be configured and arranged to stimulate nerve fibers in the dorsal roots, while avoiding stimulation of the dorsal column.

The dorsal column is typically located along a midline of the spinal cord, while the dorsal roots typically enter the spinal cord at locations that are lateral from the dorsal column. Thus, it may be an advantage to position the paddle body 502 along the midline of the spinal cord and operate at least some of the electrodes of the two or more medial columns 516 as cathodes and operate at least some of the electrodes of the lateral columns 512, 514 as anodes so that the medially-disposed cathodes provide stimulation to the dorsal column, while the laterally-disposed anodes guard against stimulation of the dorsal roots by repelling at least some of the laterally-directed stimulation. As discussed above, in alternate embodiments, the paddle body 502 can be configured and arranged to stimulate nerve fibers in the dorsal roots, while avoiding stimulation of the dorsal column.

At least some of the electrodes of the two or more medial columns 516 may be longitudinally-aligned with one another such that the electrodes form rows along the transverse axis 508. In at least some embodiments, at least some of the longitudinally-aligned electrodes of the two or more medial columns 516 are configured and arranged to operate as cathodes. In at least some embodiments, operating two or more electrodes aligned along the transverse axis 508 as cathodes enables medial-lateral current steering to be performed by providing disproportionate levels of current to the two or more cathodes aligned along the transverse axis 508. It may be an advantage to form the electrode array 510 to promote medial-lateral current steering to selectively stimulate tissue that is not located along a midline of the spinal cord. This may especially be an advantage when stimulating lower back tissue (e.g., on or around the T6 level of the spine) where target patient tissue may occur off the midline of the spinal cord.

In at least some embodiments, electrodes of the lateral columns 512, 514 are also longitudinally-aligned with one another along the transverse axis 508. In at least some embodiments, at least some of the longitudinally-aligned electrodes of the lateral columns 512, 514 are configured and arranged to operate as anodes. As discussed above, it may be an advantage to operate at least some of the electrodes of the two or more medial columns 516 as cathodes and at least some of the electrodes of the lateral columns 512, 514 as anodes to stimulate the dorsal column while also guarding against stimulation of the laterally-positioned dorsal roots.

In at least some embodiments, longitudinally-aligned anodes of the lateral columns 512, 514 are longitudinally offset from corresponding rows of cathodes of the two or more medial columns 516. As shown in FIG. 5, the electrodes of the two medial columns 516*a* and 516*b* are longitudinally aligned with one another along the longitudinal axis 506 of paddle body (i.e., in rows). Additionally, the flanking electrodes of the lateral columns 512, 514 are also shown in FIG. 5 as being aligned with one another along the longitudinal axis 506 of paddle body. In FIG. 5, the rows of electrodes of the medial columns 516 are longitudinally offset from the electrodes of the lateral columns 512, 514. Thus, when the electrodes of the medial column 516 are operated as cathodes and the electrodes of the lateral columns are operated as anodes, the corresponding anode/cathode pairs are longitudinally offset from one another (i.e., the anode/cathode pairs are not longitudinally aligned with one another).

As discussed above, the amount of center-to-center space between corresponding anodes and cathodes (i.e., anode/cathode pairs) may affect the amount of current shunting. One way to increase the center-to-center distance between corresponding cathodes and anodes is to longitudinally offset rows of cathodes from corresponding anodes. It may sometimes be desirable to increase the center-to-center distance between corresponding cathodes and anodes to reduce current shunting, particularly to dispose more electrodes on a limited surface space on the paddle body 502. This can be important for packing 32 electrode contacts onto a paddle surface, which is limited in size.

Thus, in at least some embodiments, it may be an advantage to longitudinally offset electrodes from electrodes in an adjacent column (e.g., electrodes in the medial column relative to electrodes in the lateral column) to reduce the effects of current shunting without increasing a width of the paddle body 502 (i.e., the length of the transverse axis 508). As discussed above, it may be an advantage to maintain a narrow width in order to decrease patient discomfort during implantation and operation of the paddle lead, as well as increase accessible stimulation regions.

In at least some embodiments, the paddle body 502 has a width of no more than 12 millimeters. In at least some embodiments, the paddle body 502 has a width of no more than 11 millimeters. In at least some embodiments, the paddle body 502 has a width of no more than 10 millimeters. In at least some embodiments, the paddle body 502 has a width of no more than 9 millimeters. In at least some embodiments, the paddle body 502 has a width of no more than 8 millimeters.

The electrodes of the electrode array 510 can have any suitable center-to-center spacing between adjacent electrodes in a given column, or longitudinal spacing. It will be understood that all longitudinal spacings between adjacent electrodes are measured as center-to-center distances. In at least some embodiments, each of the electrodes of the lateral column 512 are equally spaced apart longitudinally from one another (i.e., the adjacent electrodes have equal longitudinal spacings). In at least some embodiments, each of the electrodes of the lateral column 514 are equally spaced apart longitudinally from one another (i.e., the adjacent electrodes have equal longitudinal spacings). In at least some embodiments, the longitudinal spacing of adjacent electrodes of the lateral column 512 is equal to the longitudinal spacing of adjacent electrodes of the lateral column 514. In at least some embodiments, each of the electrodes of the medial column 516a are equally spaced apart longitudinally from one another (i.e., the adjacent electrodes have equal longitudinal spacings). In at least some embodiments, each of the electrodes of the medial column 516b are equally spaced apart longitudinally from one another (i.e., the adjacent electrodes have equal longitudinal spacings). In at least some embodiments, the longitudinal spacing of adjacent electrodes of the medial column 516a is equal to the longitudinal spacing of adjacent electrodes of the medial column 516b. In at least some embodiments, the longitudinal spacing of adjacent electrodes of the lateral column 512 is equal to the longitudinal spacing of adjacent electrodes of each of the lateral column 514, the medial column 516a, and the medial column 516b. In at least some embodiments, the transverse spacing between electrodes of the lateral column 512 and electrodes of the medial column 516a is equal to the transverse spacing between electrodes of the lateral column 514 and the medial column 516b.

FIGS. 6A-6C show the paddle body 502 with three different longitudinal spacings between adjacent electrodes in the electrode array. In FIGS. 6A-6C, each of the columns 512, 514, 516 has equal longitudinal spacing between adjacent electrodes. In FIG. 6A, longitudinally-adjacent electrodes are separated from one another by a first longitudinal spacing 602 between adjacent electrodes. In FIG. 6B, longitudinally-adjacent electrodes are separated from one another by a second longitudinal spacing 604 between adjacent electrodes that is greater than the first longitudinal spacing 602 between adjacent electrodes. In FIG. 6C, longitudinally-adjacent electrodes are separated from one another by a third longitudinal spacing 606 between adjacent electrodes that is greater than the second longitudinal spacing 604 between adjacent electrodes.

In at least some embodiments, the longitudinal spacing between adjacent electrodes is no greater than 7 millimeters. In at least some embodiments, the longitudinal spacing between adjacent electrodes is no greater than 6.5 millimeters. In at least some embodiments, the longitudinal spacing between adjacent electrodes is no greater than 6 millimeters. In at least some embodiments, the longitudinal spacing between adjacent electrodes is no greater than 5.5 millimeters. In at least some embodiments, the longitudinal spacing between adjacent electrodes is no greater than 5 millimeters. In at least some embodiments, the longitudinal spacing between adjacent electrodes is no greater than 4.5 millimeters.

As discussed above, current shunting may occur as spacing between adjacent electrodes is reduced. Current shunting may be used to enhance the ability to direct medial-lateral stimulation. Current shunting, however, may also cause a decrease in all or one or more portions of stimulation coverage along a given span. Computer modeling has shown that, in at least some instances, a longitudinal spacing between adjacent electrodes that is greater than six millimeters reduces current shunting to facilitate equal stimulation along the patient's rostral-caudal axis. Computer modeling also has shown that, in some instances, a longitudinal spacing that is greater than six millimeters may provide therapy (e.g., reducing back pain, or the like) when positioned at the T8 level of the patient's spine.

In some situations, enhanced control over medial-lateral stimulation (i.e., improved current steering) may outweigh the corresponding insufficiencies in complete stimulation across the rostral-caudal axis (i.e., a shorter longitudinal span of stimulation). For example, improved current steering may outweigh a shorter longitudinal span of stimulation when a patient is experiencing pain emanating from one or more discrete regions in close proximity to one another or off the midline of the spinal cord (e.g., lower back pain, or the like). Computer modeling has shown that, in at least some instances, a longitudinal spacing between adjacent electrodes that is no greater than six millimeters experiences sufficient current shunting to facilitate tuning the direction of stimulation along a medial-lateral axis. Computer modeling also has shown that, in at least some instances, such a longitudinal spacing may provide therapy (e.g., reducing back pain, or the like) when positioned at the T6 level of the patient's spine.

The electrodes can be configured into any number of columns greater than three, and any number of electrodes can be disposed in any of the columns. When the electrode array 510 includes thirty-two electrodes, many different electrode configurations are possible including, for example, two lateral columns with six electrodes each, two medial columns with six electrodes, and one medial column with eight electrodes. This configuration may simply be referred to as 6-6-8-6-6, where the number of electrodes in a column are counted from left to right. It may be helpful to use this shorthand notation. Alternately, the above configuration may be rearranged such that the eight-electrode column may be disposed in the second position (6-8-6-6-6), or the fourth position (6-6-6-8-6). Other 32-electrode configurations may include, for example 6-7-6-7-6; 5-5-6-6-5-5; 4-4-5-6-5-4-4; and 4-4-4-4-4-4-4-4. It will be understood that other rearrangements and configurations are possible, as well.

Turning now to FIG. 7A, the plurality of lead bodies are configured and arranged for insertion into one or more connectors. The plurality of lead bodies can be configured and arranged for insertion into one or more connectors in many different ways. In at least some embodiments, conductive wires extending from electrodes disposed on the paddle body can be arranged into a plurality of distinct groups, and each group disposed in the plurality of lead bodies. In at least some embodiments, each of the lead bodies is configured and arranged for direct insertion into the one or more connectors. In at least some embodiments, each of the lead bodies is configured and arranged for insertion into a splitter which, in turn, is configured and arranged for insertion into the one or more connectors. In at least some embodiments, conductive wires extend from the paddle body to a distal element that, in turn, is coupled to the lead bodies.

FIG. 7A is a schematic view of one embodiment of an electrical stimulation system 700. The electrical stimulation system 700 includes a paddle lead assembly 702. The paddle lead assembly 702 includes a paddle body 704 and lead bodies 706. An array of electrodes 708 is disposed on the paddle body 704. An array of terminals 710 is disposed on each of the lead bodies 706. The electrical stimulation system 700 also includes one or more control modules 712 and one or more connectors 714 for coupling the lead bodies 706 to the control module(s) 712. In at least some embodiments, the one or more control modules 712 includes 32 independently programmable stimulation channels. The terminals 710 are insertable into the one or more connectors 714 such that conductive wires within the lead bodies 706 electrically couple to conductive contacts disposed within one or more ports of the one or more connectors 714.

One or more conductive wires electrically couple the electrodes 708 to the terminals 710. At least a portion of the conductive wires extend within the lead bodies 706. In at least some embodiments, each electrode 708 is coupled to a single different corresponding terminal 710 on one of the lead bodies 706 via a single conductive wire. In at least some embodiments, at least one conductive wire extends along each of the lead bodies 706.

In at least some embodiments, the electrodes 708 are arranged into columns 716. In at least some embodiments, each different column 716 of electrodes is electrically coupled to terminals disposed on a different one of the lead bodies 706. In at least some embodiments, the paddle body 704 includes four columns 716 of electrodes. In at least some embodiments, each column 716 includes eight electrodes. In at least some embodiments, each of the lead bodies 706 are the same length. In at least some embodiments, at least one of the lead bodies 706 has a length that is different from at least one other of the lead bodies 706. In at least some embodiments, each of the lead bodies 706 has a different length.

When multiple lead bodies are inserted into a patient, it may be difficult for a medical practitioner to identify which proximal end of which lead body corresponds to which electrode(s). Accordingly, it may be an advantage to form the lead bodies 706 with different lengths to distinguish each lead body 706 from the other lead bodies 706, thereby facilitating identification of which lead bodies include conductive wires coupled to which electrodes. It will be understood that arranging electrodes into columns and using different lengths for each of the lead bodies can also facilitate electrode identification. Additionally (or alternatively), one or more markers can be disposed on one or more of the lead bodies 706 to facilitate electrode identification. These considerations and arrangements also apply equally to each of the below-described embodiments of the electrical stimulation system.

Any number of lead bodies 706 can be disposed on the paddle lead assembly 702 including, for example, two, three, four, or more lead bodies 706. In FIG. 7A, the paddle lead assembly 702 includes four lead bodies 706. In at least some embodiments, the number of lead bodies 706 is equal to the number of columns 716 of electrodes.

Turning now to FIG. 7B, sometimes a lead body is incompatible with a connector. For example, a lead body may include a number of terminals that exceeds a number of conductor contacts disposed in a connector. In at least some embodiments, a paddle lead assembly may include one or more lead splitters that receive lead bodies and split the conductive wires of the received lead bodies into two or more groupings disposed in splitter bodies that are compatible with, for example, conventional connectors.

FIG. 7B is a schematic view of a second embodiment of an electrical stimulation system 730. The electrical stimulation system 730 includes a paddle lead assembly 732. The paddle lead assembly 732 includes a paddle body 734 and lead bodies 736. An array of electrodes 738 is disposed on the paddle body 734. An array of terminals 740 is disposed on each of the lead bodies 736. The electrical stimulation system 730 also includes lead splitters 742. The lead splitters 742 include connectors 744 and splitter lead bodies 746. In at least some embodiments, the connectors 744 are female connectors. Splitter terminal arrays 748 are disposed on the splitter lead bodies 746. The electrical stimulation system 730 may also include one or more control modules 712 and the one or more connectors 714 for coupling the splitter bodies 744 to the control module(s) 712.

Conductive wires (not shown) extending within the lead splitters 742 electrically couple connector contacts within the splitter connectors 744 to terminals of the splitter terminal arrays 748. The splitter conductive wires are split into multiple groupings of conductive wires. Each grouping of conductive wires extends within a different splitter body 744. For example, in at least some embodiments, the lead bodies 736 each have sixteen terminals 740 and the splitter terminal arrays 748 each have eight terminals. Thus, in at least some embodiments, a thirty-two electrode paddle lead 732 may be coupled to two lead bodies 736 each having sixteen terminals 740, and each of two lead splitters 742 may receive one of the sixteen-terminal lead bodies 736 and couple the sixteen terminals 740 of the received lead body 736 to two splitter terminal arrays 748 each having eight terminals and each configured and arranged for insertion into the one or more connectors 714 such that conductive wires within the splitter bodies 744 electrically couple to conductive contacts disposed within one or more ports of the one or more connectors 714.

FIG. 7B shows each lead splitter 742 including two splitter lead bodies 746. It will be understood that the lead splitters 742 may include any number of splitter lead bodies 746 including, for example, three, four, five, six, seven, eight, nine, ten, or more splitter lead bodies 746. Splitter terminals 748 may be disposed on all, or a portion, of the splitter lead bodies 746.

In FIG. 7B, the splitter lead bodies 746 of one of the lead splitters 742 are identified as 746a and 746b. In at least some embodiments, at least one of the splitter lead bodies 746 has a length that is different from at least one other of the splitter lead bodies 746. For example, in at least some embodiments, the splitter lead bodies 746a and 746b have different lengths. As discussed above, when multiple lead bodies and lead splitters are inserted into a patient, it may be difficult for a medical practitioner to identify which proximal end of which splitter lead body 746 corresponds to which electrode(s). Thus, it may be an advantage to form the splitter lead bodies 746 with different lengths to distinguish each splitter lead bodies 746 from the other splitter lead bodies 746, thereby facilitating identification of which splitter lead bodies 746 includes conductive wires coupled to which electrodes. Additionally (or alternatively), one or more markers can be disposed on one or more of the splitter lead bodies 746 to distinguish each splitter lead bodies 746 from the other splitter lead bodies 746.

Turning now to FIG. 7C, in at least some embodiments the electrical stimulation system includes an intermediate extension element and a plurality of lead bodies disposed proximally to the intermediate extension element. In at least some embodiments, the intermediate extension element is coupled to the lead bodies via one or more junctions.

Conductive wires extending within the extension element are divided at the junction into multiple distinct groupings of conductive wires. Each distinct grouping of conductive wires extends within a different proximal element. At least one of the lead bodies is configured and arranged to couple to a connector such that conductive wires within the lead body electrically couple to connector contacts disposed within one or more ports of the connector.

FIG. 7C is a schematic view of a third embodiment of an electrical stimulation system 770. The electrical stimulation system 770 includes a paddle lead assembly 772. The paddle lead assembly 772 includes a paddle body 774 and a lead body arrangement 776. An array of electrodes 778 is disposed on the paddle body 774. The lead body arrangement 776 includes an intermediate extension element 780 coupled to the paddle body 774, a plurality of lead bodies 782, and a junction 784 coupling the intermediate extension element 780 to the plurality of lead bodies 782. An array of terminals 786 is disposed on at least one of the plurality of lead bodies 782. The electrical stimulation system 770 also includes the one or more control modules 712 and the one or more connectors 714 for coupling the proximal lead bodies 782 to the control module(s) 712.

In at least some embodiments, the extension element 708 has a length that is substantially greater than a length of each of the lead bodies 782. In at least some embodiments, at least one of the lead bodies 782 has a length that is different than at least one other of the lead bodies 782. When multiple lead bodies 782 and junctions 784 are inserted into a patient, it may be difficult for a medical practitioner to identify which proximal end of which lead body corresponds to which electrode(s). Thus, it may be an advantage to form the lead bodies 782 with different lengths to distinguish each of the lead bodies 782 from one another, thereby facilitating identification of which lead body 782 includes conductive wires coupled to which electrodes. Additionally (or alternatively), one or more markers can be disposed on one or more of the lead bodies 782 to distinguish each lead body 782 from the other lead bodies 782.

It may be an advantage to use a paddle lead assembly having a single extension element extending from the paddle body 774 because using a single extension element may reduce patient discomfort during insertion or during the implantation period of the electrical stimulation system 770. When multiple lead bodies are inserted into a patient such that each of the lead bodies extends the entire distance between the paddle body and the control module, multiple tunnels may be bored through patient tissue. Each tunnel may cause patient discomfort or lead to potential complications during implantation. Additionally, in order to maintain precise positioning of paddle bodies during operation, some lead bodies may be anchored to patient tissue. Each anchoring may also cause patient discomfort or lead to potential complications during implantation. It may, therefore, be an advantage to only anchor a single extension element to patient tissue in proximity to the paddle body instead of anchoring a plurality of lead bodies.

In at least some embodiments, the cross-sectional profile of the extension element may be reduced to further reduce patient discomfort. In at least some embodiments, the extension element may be formed from a single extrusion of one or more polymers (e.g., ethylene tetrafluoroethylene, or the like) coated with one or more layers of biocompatible, biostable insulating material (e.g., polyurethane, silicone, or the like).

Conductive wires can be disposed in the extension element 780 in any configuration. It may be an advantage to extend conductive wires along the intermediate extension element 780 arranged into distinct (by sight, by touch, or the like) groupings that correspond to each of the plurality of lead bodies 782. In at least some embodiments, one or more dividers may extend along all, or a portion, of the intermediate extension element 780 to separate one or more of the groupings from one another. FIG. 8A is a schematic transverse cross-sectional view of one embodiment of an arrangement of dividers 802 disposed along the intermediate extension element 780. FIG. 8B is a schematic transverse cross-sectional view of a second embodiment of an arrangement of dividers 802 disposed along the intermediate extension element 780. FIG. 8C is a schematic transverse cross-sectional view of a third embodiment of an arrangement of dividers 802 disposed along the intermediate extension element 780.

The transverse profile of the intermediate extension element 780 can be any geometric or non-geometric shape including, for example, round, oval, rectangular, rounded rectangular, or the like. In preferred embodiments, the transverse profile of the extension element is formed so as to reduce patient discomfort. In at least some embodiments, the intermediate extension element 780 does not receive a stylet. In at least some embodiments, the intermediate extension element 780 does not couple directly to the one or more connectors 714.

In at least some embodiments, the plurality of lead bodies 782 each couple to the junction 784 such that the lead bodies 782 are stacked into two or more layers. FIG. 9A is a schematic transverse cross-sectional view of one embodiment of the lead bodies 782 extending within the junction 784. The lead bodies 782 are arranged into two layers 902 and 904. It will be understood that the lead bodies 782 can be arranged into any number of layers, and each layer may include any number of lead bodies 782.

In at least some embodiments, the lead bodies 782 couple to the junction 784 such that the lead bodies 782 are arranged into a single layer. FIG. 9B is a schematic transverse cross-sectional view of one embodiment of the lead bodies 782 extending within the junction 784. The lead bodies 782 are arranged into a single layer 906. It may be an advantage to couple the lead bodies 782 to the junction 784 in a single layer because a single layer of lead bodies 782 may produce less patient discomfort than multiple layers. It may also be an advantage to couple the lead bodies 782 to the junction 784 in a single layer because the arrangement of the lead bodies 782 may be configured in a manner that is similar to the arrangement of the electrodes 778, thereby facilitating identification of which lead body includes terminals coupled to which electrodes, or columns of electrodes.

Figure 10A:
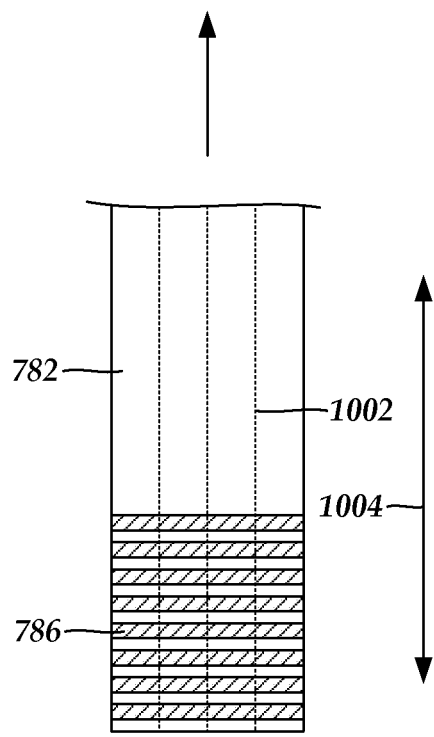
FIG. 10A is a schematic side view of one embodiment of proximal ends of lead bodies of a lead body arrangement, the lead bodies coupled together by weakened regions, according to the invention.
Figure 10B:
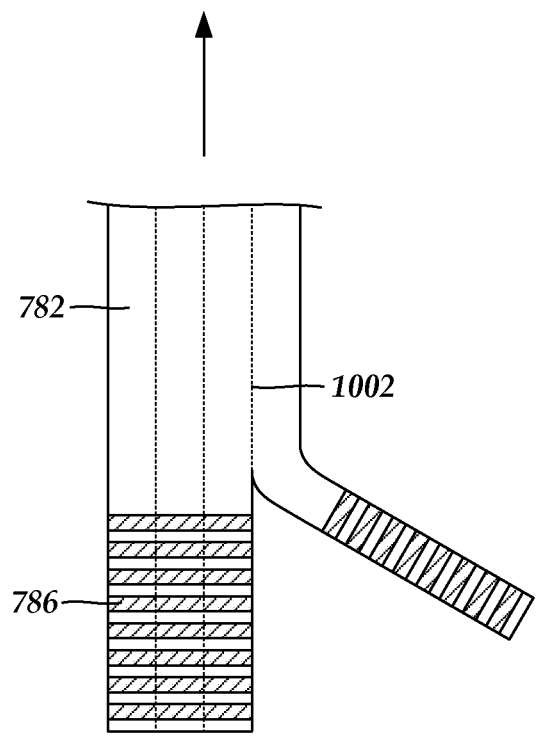
FIG. 10B is a schematic side view of one embodiment of proximal ends of the lead bodies of FIG. 10A, with one of the lead bodies separated from the other lead bodies due to separation along a weakened region, according to the invention.

Turning now to FIGS. 10A and 10B, in at least some embodiments the lead bodies 782 are at least partially coupled together along at least a portion of a longitudinal axis of the lead bodies 782. In at least some embodiments, the lead bodies 782 are coupled together such that one or more weakened regions (e.g., perforations, or the like) are formed along at least a portion of the coupled portions. In at least some embodiments, one or more of the lead bodies 782 can be separated from the other lead bodies 782 along one or more of the weakened regions and inserted into a connector. It will be understood that the lead bodies 706, or the lead splitter bodies 746 can also be similarly coupled together by one or more weakened regions.

FIG. 10A is a schematic side view of one embodiment of proximal ends of the lead bodies 782. The lead bodies 782 are arranged in a single layer such that the lead bodies 782 are in a side-by-side configuration. The lead bodies 782 are coupled together by one or more weakened regions, such as weakened region 1002 extending along a longitudinal axis, shown in FIG. 10A as an arrow 1004. In at least some embodiments, one or more of the weakened regions may be separated to partially detach one or more of the lead bodies 782 from one or more other of the lead bodies 782.

FIG. 10B is a schematic side view of one embodiment of proximal ends of the lead bodies 782. One of the weakened regions 1002 has been separated along a proximal-most portion of the weakened region to partially separate one of the lead bodies 782 from the other lead bodies 782. In at least some embodiments, the separated lead body 782 can be inserted into a connector (e.g. of a control module, a lead extension, or the like). In at least some embodiments, the one or more weakened regions 1002 can be separated by a medical practitioner during implantation of the electrical stimulation system 770. In at least some embodiments, the one or more weakened regions 1002 can be separated after the paddle lead assembly 772 is inserted into a patient.

Figure 11:
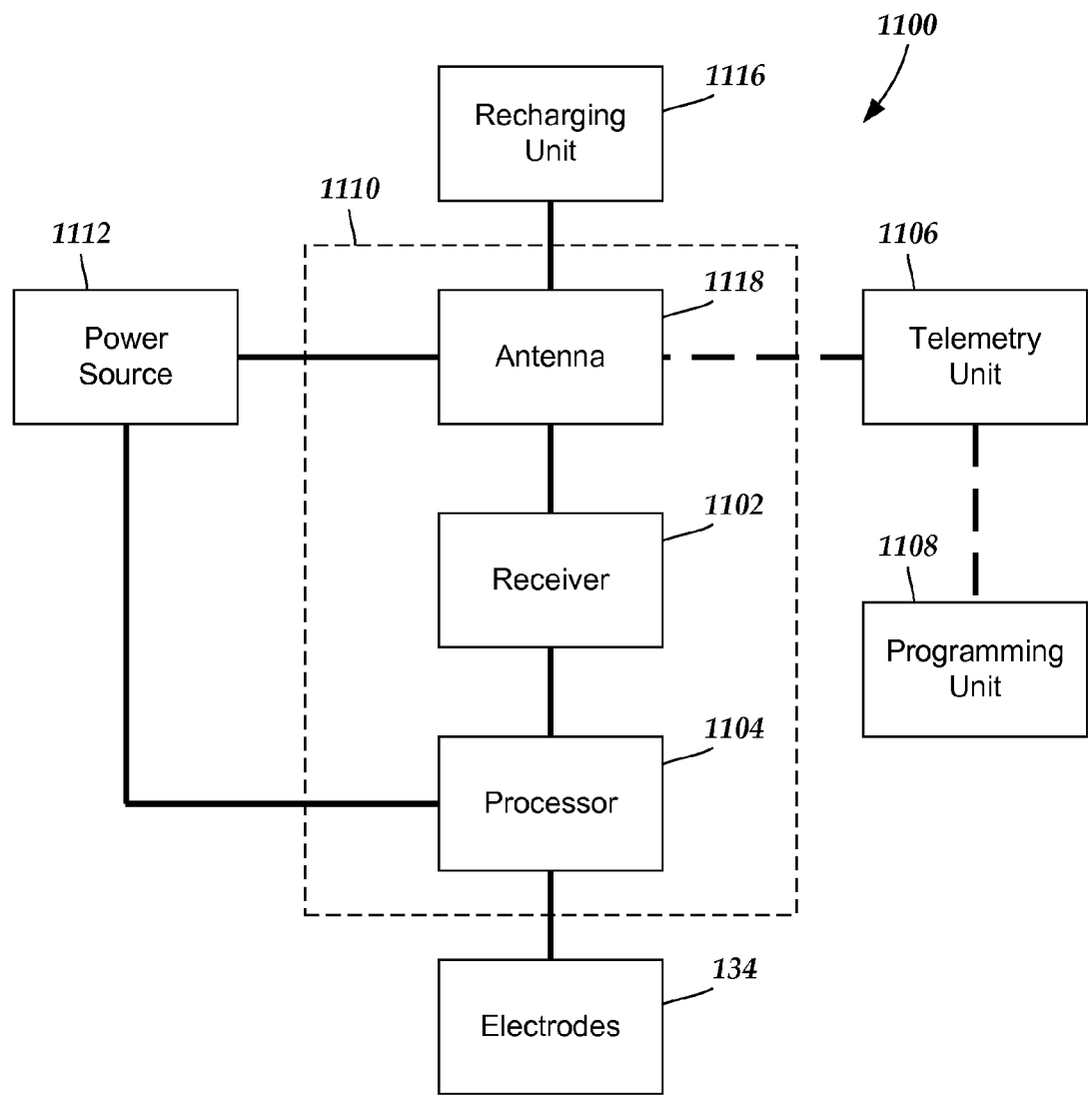
FIG. 11 is a schematic overview of one embodiment of components of a stimulation system, including an electronic subassembly disposed within a control module, according to the invention.

FIG. 11 is a schematic overview of one embodiment of components of an electrical stimulation system 1100 including an electronic subassembly 1110 disposed within a control module. It will be understood that the electrical stimulation system can include more, fewer, or different components and can have a variety of different configurations including those configurations disclosed in the stimulator references cited herein.

Some of the components (for example, power source 1112, antenna 1118, receiver 1102, and processor 1104) of the electrical stimulation system can be positioned on one or more circuit boards or similar carriers within a sealed housing of an implantable pulse generator, if desired. Any power source 1112 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 1118 or a secondary antenna. The external power source can be in a device that is mounted on the skin of the user or in a unit that is provided near the user on a permanent or periodic basis.

If the power source 1112 is a rechargeable battery, the battery may be recharged using the optional antenna 1118, if desired. Power can be provided to the battery for recharging by inductively coupling the battery through the antenna to a recharging unit 1116 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 1104 is generally included to control the timing and electrical characteristics of the electrical stimulation system. For example, the processor 1104 can, if desired, control one or more of the timing, frequency, strength, duration, and waveform of the pulses. In addition, the processor 1104 can select which electrodes can be used to provide stimulation, if desired. In some embodiments, the processor 1104 may select which electrode(s) are cathodes and which electrode(s) are anodes. In some embodiments, the processor 1104 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 1108 that, for example, allows modification of pulse characteristics. In the illustrated embodiment, the processor 1104 is coupled to a receiver 1102 which, in turn, is coupled to the optional antenna 1118. This allows the processor 1104 to receive instructions from an external source to, for example, direct the pulse characteristics and the selection of electrodes, if desired.

In one embodiment, the antenna 1118 is capable of receiving signals (e.g., RF signals) from an external telemetry unit 1106 which is programmed by a programming unit 1108. The programming unit 1108 can be external to, or part of, the telemetry unit 1106. The telemetry unit 1106 can be a device that is worn on the skin of the user or can be carried by the user and can have a form similar to a pager, cellular phone, or remote control, if desired. As another alternative, the telemetry unit 1106 may not be worn or carried by the user but may only be available at a home station or at a clinician's office. The programming unit 1108 can be any unit that can provide information to the telemetry unit 1106 for transmission to the electrical stimulation system 1100. The programming unit 1108 can be part of the telemetry unit 1106 or can provide signals or information to the telemetry unit 1106 via a wireless or wired connection. One example of a suitable programming unit is a computer operated by the user or clinician to send signals to the telemetry unit 1106.

The signals sent to the processor 1104 via the antenna 1118 and receiver 1102 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 1100 to cease operation, to start operation, to start charging the battery, or to stop charging the battery. In other embodiments, the stimulation system does not include an antenna 1118 or receiver 1102 and the processor 1104 operates as programmed.

Optionally, the electrical stimulation system 1100 may include a transmitter (not shown) coupled to the processor 1104 and the antenna 1118 for transmitting signals back to the telemetry unit 1106 or another unit capable of receiving the signals. For example, the electrical stimulation system 1100 may transmit signals indicating whether the electrical stimulation system 1100 is operating properly or not or indicating when the battery needs to be charged or the level of charge remaining in the battery. The processor 1104 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A paddle lead assembly for providing electrical stimulation of patient tissue, the paddle lead assembly comprising:
   a paddle body having a length along a longitudinal axis and a width along a lateral axis transverse to the longitudinal axis, wherein the width of the paddle body is no more than nine millimeters;
   a plurality of electrodes, the plurality of electrodes arranged into at least four columns extending parallel with the longitudinal axis of the paddle body, the at least four columns comprising two lateral columns and at least two medial columns disposed therebetween with the two lateral columns flanking the at least two medial columns, wherein the electrodes of the at least two medial columns are arranged into rows aligned along the transverse axis, wherein the electrodes of the two lateral columns are each longitudinally offset from the rows of electrodes of the at least two medial columns, wherein each of the at least four columns of electrodes has an equal number of electrodes, and wherein each of the at least four columns of electrodes comprises at least five electrodes;
   a plurality of lead bodies coupled to the paddle body;
   an array of terminals disposed on each of the plurality of lead bodies; and
   a plurality of conductive wires, each conductive wire coupling one of the electrodes to at least one terminal of at least one of the terminal arrays.

2. Th paddle lead assembly of claim 1, wherein the electrodes of the paddle body are arranged into four columns.

3. The paddle lead assembly of claim 1, wherein each of the at least four columns comprises eight electrodes.

4. The paddle lead assembly of claim 1, wherein at least one of the electrodes of each of the at least two medial columns is configured and arranged to function as one of a cathode or an anode.

5. The paddle lead assembly of claim 1, wherein each of the columns of electrodes has equal longitudinal center-to-center spacing between longitudinally-adjacent electrodes.

6. The paddle lead assembly of claim 5, wherein the longitudinal center-to-center spacing between longitudinally-adjacent electrodes is greater than six millimeters.

7. The paddle lead assembly of claim 6, wherein each of the at least hour columns comprises eight electrodes.

8. The paddle lead assembly of claim 1, wherein the plurality electrodes comprises thirty-two electrodes, and wherein a total number of terminals disposed collectively on each of the arrays of terminals is thirty-two terminals.

9. The paddle lead assembly of claim 1, wherein at least two of the plurality of lead bodies are coupled to one another along at least one perforated region.

10. The paddle lead assembly of claim 1, wherein the paddle body has a length along the lateral axis that is no greater than 12millimeters.

11. The paddle lead assembly of claim 1, wherein the plurality of electrodes comprises thirty-two electrodes arranged into four columns each having eight electrodes, and wherein each of the four columns of electrodes has equal longitudinal center-to-center spacing between longitudinally-adjacent electrodes.

12. An electrical stimulating system comprising:
   the paddle lead assembly of claim 1;
   at least one control module configured and arranged to electrically couple to each of the electrodes, each of he at least one control module comprising
      a housing, and
      an electronic subassembly disposed in the housing; and
   a connector assembly for receiving at least one of the lead bodies, the connector assembly comprising
      a connector housing defining a port at a distal end of the connector housing, the port configured and arranged for receiving a portion of one of the plurality of lead bodies, and
      a plurality of connector contacts disposed in the connector housing, the connector contacts configured and arranged to couple to at least one of the plurality of terminals disposed on each of the at least one of the lead bodies.

13. The electrical stimulating system of claim 12, wherein the at least one control module has 32 independently programmable stimulation channels for delivering constant current stimulus pulses.

14. The electrical stimulating system of claim 12, wherein the housing of the at least one control module is programmable to be an anode (ON) or be programmed OFF.

15. The electrical stimulating system of claim 12, wherein the connector is disposed on the control module.

16. The electrical stimulating system of claim 12, further including a lead extension having a distal end and at least one proximal end, the connector disposed on the distal end of the lead extension.

17. The electrical stimulating system of claim 16, wherein at least one of the proximal ends of the lead extension is configured and arranged for insertion into another connector.

18. The electrical stimulating system of claim 12, wherein the paddle lead assembly comprises two lead bodies, each of the two lead bodies having 16 terminals and two lead splitters, wherein each of the two lead splitters comprises two splitter lead bodies, and wherein each of the two lead splitter bodies comprises eight terminals.

19. The electrical stimulating system of claim 12, wherein the paddle lead assembly comprises an intermediate extension element coupling the paddle body to a junction, and wherein the four lead bodies are each coupled to the junction.

20. The electrical stimulating system of claim 19, wherein a plurality of intermediate-extension-element conductors extend along it length of the intermediate extension element, and wherein the intermediate extension element comprises at least one divider extending along the length of the intermediate extension, the at least one divider configured and arranged to separate the plurality of intermediate-extension-element conductors into at least two groupings of intermediate-extension-element conductors.

21. A method for treating middle or upper back pain, the method comprising:

providing the paddle lead assembly of claim 1;

insertingthepaddlebodyofthepaddleleadassemblyinto an epidural space of a patient with at least some of the electrodes disposed in proximity to the thoracic region of the patient's spine; and providing current to at least some of the electrodes from an electrically coupled pulse generator.

22. The method of claim 21, wherein inserting the paddle body of the paddle lead assembly into the epidural space of the patient comprise inserting the paddle body into the epidural space of the patient such that the longitudinal axis of the paddle body aligns with the patient's spinal cord.

23. The method of claim 21, wherein providing current to at least some of the electrodes from an electrically coupled pulse generator comprises providing current to at least one of the rows of electrodes disposed in the at least two medial columns such that those electrodes operate as cathodes, and providing current to at least one electrode of each of the lateral columns such that those electrodes operate as anodes, and wherein the electrodes operating as anodes are longitudinally offset along the paddle body from the electrodes operating as cathodes.

24. The method of claim 21, wherein providing current to at least one of the rows of electrodes disposed in the at least two medial columns such that those electrodes operate as cathodes comprises providing current to a first cathode and a second cathode of one of the rows of electrodes such that the first cathode receives a different level of current than the second cathode.

25. The method of claim 21, wherein inserting the paddle body of the paddle lead assembly into the epidural space of the patient with at least some of the electrodes disposed in proximity to the thoracic region of the patient's spine comprises inserting the paddle body of the paddle lead assembly into the epidural space of the patient with at least some of the electrodes disposed in proximity to the T8level of the patient's spine.

\* \* \* \* \*